(12) United States Patent
Seaver

(10) Patent No.: US 7,619,725 B1
(45) Date of Patent: Nov. 17, 2009

(54) OPTICALLY AMPLIFIED CRITICAL WAVELENGTH REFRACTOMETER

(75) Inventor: George A. Seaver, Cataumet, MA (US)

(73) Assignee: Sealite Engineering, Inc., Cataumet, MA (US)

(*) Notice: Subject to any disclaimer, the term of this patent is extended or adjusted under 35 U.S.C. 154(b) by 0 days.

(21) Appl. No.: 12/152,220

(22) Filed: May 12, 2008

(51) Int. Cl.
    *G01N 21/41* (2006.01)
(52) U.S. Cl. ...................... 356/137; 356/128
(58) Field of Classification Search ......... 356/128–137, 356/432–440
    See application file for complete search history.

(56) References Cited

U.S. PATENT DOCUMENTS

| | | | | |
|---|---|---|---|---|
| 3,975,084 | A | * | 8/1976 | Block .......................... 356/335 |
| 4,529,319 | A | * | 7/1985 | Muller ........................ 356/432 |
| 4,699,511 | A | | 10/1987 | Seaver |
| 4,746,179 | A | * | 5/1988 | Dahne et al. .................. 385/12 |
| 4,822,135 | A | * | 4/1989 | Seaver ......................... 385/13 |
| 4,830,502 | A | * | 5/1989 | Saito et al. ................... 356/432 |
| 5,125,740 | A | * | 6/1992 | Sato et al. .................... 356/128 |
| 5,309,214 | A | * | 5/1994 | Hashimoto ................... 356/128 |

OTHER PUBLICATIONS

Millard et al., An Index of Refraction Algorithm for Seawater Over Temperature, Pressure, Salinity, Density, and Wavelength, Deep-Sea Research, 1990, pp. 1909-1926, vol. 37, No. 12, Published in: Great Britain.

* cited by examiner

*Primary Examiner*—Sang Nguyen
(74) *Attorney, Agent, or Firm*—Patent Law Office of David G. Beck

(57) ABSTRACT

A critical wavelength refractometer is provided. A broadband light source (413) is optically coupled to a sensor (401), the sensor having at least one sensing surface (407). As the light from the broadband light source passes through the sensor, it undergoes multiple internal reflections against the sensing surface. Due to the index of refraction of the material in contact with the sensing surface, a portion of the light passing through the sensor is reflected while a second portion of the light is transmitted through the sensing surface and into the material. A detector (421) coupled to the sensor measures the spectral intensity of the light that passes completely through the sensor after having undergone the multiple internal reflections against the sensing surface. A microprocessor (423) coupled to the detector determines the critical wavelength based on the spectral intensity measurement, thereby allowing the index of refraction of the material to be determined.

19 Claims, 6 Drawing Sheets

OPTICALLY AMPLIFIED CRITICAL WAVELENGTH REFRACTOMETER

FIELD OF THE INVENTION

The present invention relates generally to index of refraction sensors and, more particularly, to a critical wavelength refractometer.

BACKGROUND OF THE INVENTION

Physical oceanography studies have used the index of refraction as a means of determining the density of seawater for decades, although only recently have practical instruments with suitable accuracy been developed. In general terms, these instruments use one of three refractometry principles; critical reflection measurements at a single wavelength, speed of light measurements at a single wavelength, and critical reflection measurements using a broadband source.

In conventional refractometers, the variation of the critical angle is measured as a function of the external index of refraction, the measurement being performed using a monochromatic source. This method, generally accurate to the fifth decimal place, is used in commercial laboratory instruments as well as in industrial process control. In the 1980's an in-situ device was made based on this principle which used a solid-state beam-position indicator and was accurate to the sixth decimal place; however, the mechanical nature of angular measurements make them subject to errors from oceanic pressure and temperature changes.

The index of refraction is defined as the ratio of the speed of light in vacuum to that in the medium in question. Unfortunately, this parameter cannot be easily measured. However, with the help of a reference beam with which to compare the speed of the sensing beam, the phase difference between the two beams can be determined and becomes a very sensitive measure of the index of refraction. In the early 1990's a modified interferometer was used to measure the index of refraction to the seventh decimal place in the laboratory and to the sixth decimal place in-situ. As these interferometric methods measure the index of refraction relative to a fixed value in the reference beam, pressure and temperature changes can affect the result and thus limit the overall in-situ accuracy to the $10^{-6}$ range.

The third refractometry principle spectrally decomposes a broadband 'white' sensing beam reflected at the nominal critical angle from a flat window and determines the wavelength at critical reflection. This method exploits the differing dispersions of the indices of the glass window and the water that is external to the window. The primary benefits of this method are in its simplicity and its ability to perform in-situ measurements with an accuracy in the $10^{-6}$ range.

Although all of the afore-described techniques provide means for measuring the index of refraction of seawater, none of them provide the desired level of accuracy for an in-situ oceanographic instrument. Accordingly, what is needed in the art is an in-situ oceanographic instrument that can simply and reliably measure the index of refraction of seawater to the desired level of accuracy. The present invention provides such an in-situ instrument.

SUMMARY OF THE INVENTION

The present invention provides a method and apparatus for determining the index of refraction of a material. The critical wavelength refractometer of the invention employs a broadband light source that is optically coupled to a sensor, typically with a collimating optic interposed between the light source and the sensor. The sensor can be fabricated from silica, germanium doped silica, or other material. The material to be studied is in contact with at least one sensing surface of the sensor. As the light from the broadband light source passes through the sensor, it undergoes multiple internal reflections against the sensing surface. Due to the index of refraction of the material in contact with the sensing surface, a portion of the light passing through the sensor is reflected while a second portion of the light is transmitted through the sensing surface and into the material. These portions are characterized by their wavelength. A detector, e.g., a spectrograph, coupled to the sensor measures the spectral intensity of the light that passes completely through the sensor after having undergone the multiple internal reflections against the sensing surface. A microprocessor coupled to the detector determines the wavelength, called the critical wavelength, separating the first and second portions of light. This is based on the spectral intensity measurement, thereby allowing the index of refraction of the material to be determined.

In one embodiment, the sensor is comprised of a sensor window. The sensing surface of the sensor window is preferably the lower window surface, or a portion of the lower window surface. Preferably the upper and lower window surfaces are parallel to within 10 arc seconds. In one configuration a first prism is used to couple the broadband light source to the sensor window and a second prism is used to couple the sensor window to the detector.

In another embodiment, the sensor is comprised of a sensor probe in which both the upper and lower probe surfaces are sensing surfaces, the front probe face provides both an entrance surface and an exit surface, and the end probe face is mirrored.

In another aspect of the invention, a beam splitter is interposed between the broadband light source and the sensor, the beam splitter dividing the incident light into a reference beam and a sensing beam. The sensing beam is coupled to the sensor where it undergoes multiple internal reflections against the sensing surface(s). The reference beam does not interact with the external material or the sensing surface(s), thereby providing a means for monitoring intensity and/or spectral variations in the output of the light source. The reference beam can be coupled to a second detector, e.g., a spectrograph, or multiplexing can be used to couple both the sensing beam and the reference beam to a single detector. Preferably a polarizing beam splitter is used, thus further enhancing the sensitivity of the sensing beam.

A further understanding of the nature and advantages of the present invention may be realized by reference to the remaining portions of the specification and the drawings.

DESCRIPTION OF THE SPECIFIC EMBODIMENTS

Figure 1:
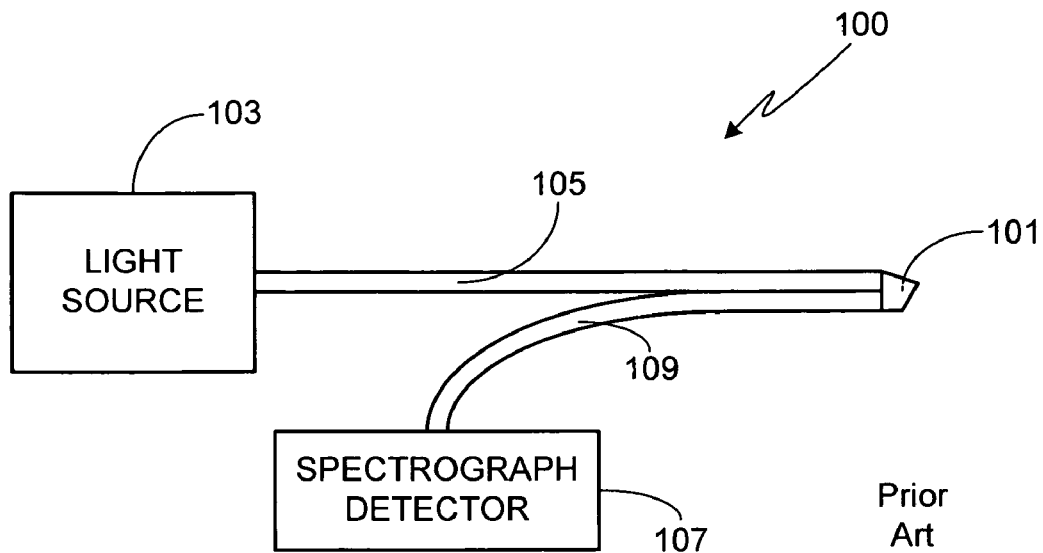
FIG. 1 illustrates a critical wavelength refractometer according to the prior art.

FIG. 1 is an illustration of a critical wavelength refractometer in accordance with the prior art, a full description of which is provided in U.S. Pat. No. 4,699,511, entitled Refraction Sensor, the specification of which is incorporated herein. As shown, refractometer 100 is comprised of a probe that includes a prism-shaped sensor 101. Sensor 101 is coupled to a broadband white radiant energy light source 103 by at least one optical fiber 105, and coupled to a spectrograph detector 107 by at least one optical fiber 109.

Figure 2:
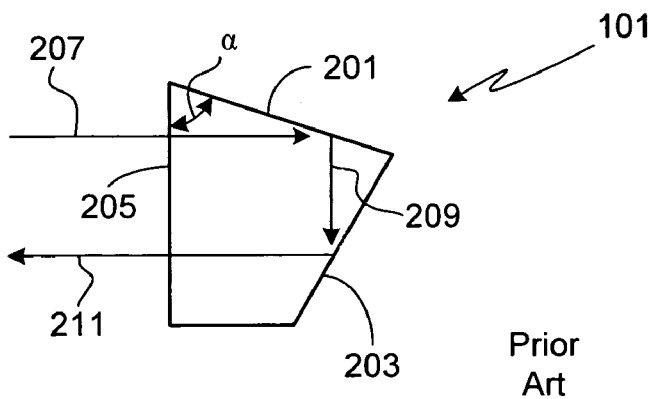
FIG. 2 provides further detail regarding the prism-shaped sensor of the critical wavelength refractometer of FIG. 1.

As shown in detail in FIG. 2, prism-shaped sensor 101 includes a ground and polished sensing face 201, a mirrored reflecting face 203, and an incident face 205. Angle $\alpha$, measured between faces 201 and 205, is chosen along with the wavelength range of light source 103 and the material comprising the prism-shaped sensor 101 to cover the index of refraction range of interest for the material to be monitored, i.e., the material in contact with sensing face 201.

In use, the light emitted by light source 103 passes through optical fiber 105, the light being schematically illustrated in FIG. 2 as light ray 207. A band of broadband light ray 207 is reflected by sensing face 201 as ray 209, this portion being dependent upon the wavelength of the light and the index of refraction of the material (e.g., seawater) that is in contact with sensing face 201. Ray 209 is reflected by mirrored reflecting face 203 as ray 211. Ray 211 passes through optical fiber 109 to spectrograph detector 107 which, in turn, determines the wavelength band and the band edge of the light that has passed through sensor 101. By measuring the wavelength of the band edge of the reflected ray, the index of refraction of the material in contact with the sensing face can be determined.

The sensitivity of the critical wavelength refractometry method increases as the optical dispersion of the sensor and the sample (e.g., seawater) approach each other. This goal can be accomplished by choosing an optical glass for the sensor that has a dispersion closer to that of the sample material, for example fabricating the sensor from Crown glass or fused quartz. This goal can also be achieved by utilizing that part of the optical spectrum where the dispersions of the sensor and the sample material naturally converge, typically towards the longer red and infrared wavelengths. Unfortunately, this approach causes the band edges to become shallower and noisier, leaving the signal-to-noise ratio only slightly improved.

In order to achieve the dynamic range necessary for oceanographic research, preferably on the order of 2 to 3 parts in the seventh decimal place, the present invention utilizes a modified critical wavelength refractometry technique in which the sensing light ray undergoes multiple reflections against the sensing face of the optical sensor. With each additional reflection of the incident light ray on the sensing face, further transmission losses occur for those wavelengths that were partially transmitted into the sample, e.g., the seawater, on earlier reflections. This increases the resultant spectral intensity fall-off with wavelength and, thereby, improves the steepness of the band edge. Additionally, due to the steeper and linear band edge, the task of fitting to resolve the critical wavelength is simpler, faster and offering higher resolution.

Figure 3:
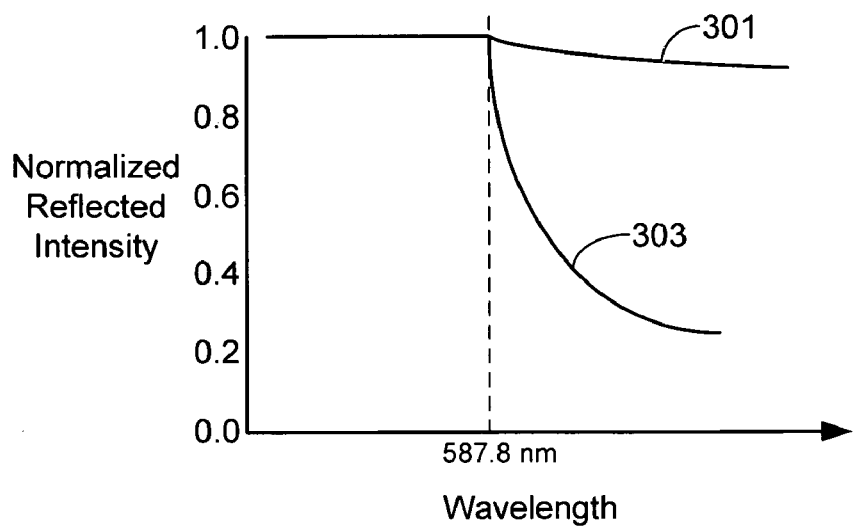
FIG. 3 graphically illustrates the benefits offered by the multi-reflection approach of the present invention over the single reflection critical wavelength refractometer of the prior art.

FIG. 3 graphically illustrates the benefits of the present invention. Curve 301 shows the experimental spectral intensity of the band edge for the case of a single reflection while curve 303 shows the same measurement after eight reflections. As shown, the optical amplification provided by the multi-reflection approach of the present invention achieves a much sharper, and thus more easily resolved, band edge.

Figure 4:
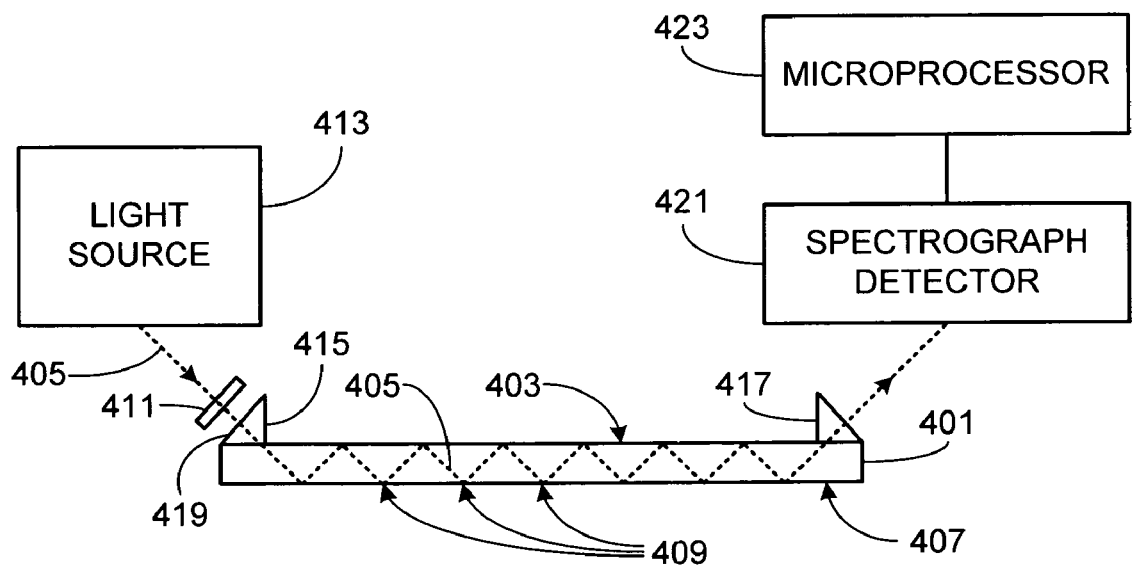
FIG. 4 illustrates the primary elements of a refractometer designed in accordance with the invention.

FIG. 4 illustrates the primary elements of a refractometer designed in accordance with the invention. The refractometer includes a sensing element 401, also referred to herein as a sensor window or simply as the sensor. In a preferred embodiment, sensor window 401 is 2 millimeters thick with the upper and lower surfaces parallel to within 10 arc seconds (i.e., 0.003 degrees). As the refractometer of the invention is preferably used to determine the index of refraction of seawater, preferred sensor materials include, but are not limited to, silica, crown glass, flint glass and germanium doped silica.

The upper surface 403 of sensor 401 is preferably exposed to air, thus providing total internal reflection of light beam 405 as it passes through the window. The lower surface 407 of sensor 401 is exposed to the material to be tested, typically seawater. It will be appreciated that upper surface 403 can be exposed to an environment other than air as long as light beam 405 is undergoes total reflection. For example, a reflective coating can be applied to surface 403 in order to achieve the desired reflectivity. In the illustrated embodiment, the light beam impinges on, and is reflected by, the sensing surface 407 at seven locations 409. It will be appreciated that the invention is not limited to a sensor with seven sensing points 409, rather the sensor can utilize more or less sensing locations, depending upon the desired measurement accuracy. The inventor has found, however, that for a sensing light beam with a divergence of approximately 0.02 degrees, little is gained by having more than eight sensing points 409.

Source 413, which provides broadband light beam 405, can be an incandescent source, a light emitting diode (LED), or other source type. As precise control over the beam's angle of incidence with respect to the sensor and the sensing surface 407 is required in order to achieve the desired level of accuracy, broadband light beam 405 from source 413 is collimated, typically using an optical collimating element 411 interposed between source 413 and the sensor. Light beam 405 is preferably coupled to sensor 401 using a small, triangular prism 415. In at least one embodiment, an optical fiber couples source 413 to prism 415, typically with collimating optical element 411 interposed between the exit facet of the fiber and prism 415. After passing through sensor 401, preferably light beam 405 exits the sensor window via a second triangular prism 417. Although sensor window 401 and prisms 415/417 can be fabricated as a single element, preferably they are individually fabricated and then bonded together using an optical epoxy. Prism 415 is designed so that light beam 405 is substantially perpendicular to prism entrance surface 419.

Sensing beam 405, after passing through sensor window 401 and undergoing multiple reflections at the interface of the sensing surface 407 and the external sample material, exits the sensor via prism 417 and enters a spectrographic detector 421. The portion of the light beam between prism 417 and spectrograph 421 can either pass through free space, or be guided using an optical fiber. If optical fibers are used to couple light source 413 and spectrograph 421 to the sensor, the sensor can be located a remote distance from the support subsystems (e.g., spectrograph, microprocessor, light source).

Spectrograph 421 measures the intensity as a function of wavelength for the light beam that has passed through sensor 401, this quantity also referred to herein as spectral intensity. This data is sent to a microprocessor 423 which, in turn, determines the band edge, also referred to as the critical wavelength. The band edge is the wavelength at which the intensity of the reflected light beam undergoes an abrupt change. For example, in the graph given in FIG. 3, the critical wavelength is 587.8 nanometers. The microprocessor then calculates the index of refraction of the external material (e.g., seawater) based on the critical wavelength, the angle of incidence of light beam 405 on sensing surface 407, and the known index of refraction of the sensor using Snell's law. The microprocessor can also calculate the salinity of the seawater, given the temperature and pressure, as well as the density of the seawater, given the conductivity of the material. Note that microprocessor 423 can be either external or internal to spectrograph 421. Additionally and as previously noted, microprocessor 423 can be either co-located with, or remote from, sensor 401.

Another advantage of an instrument designed to utilize the elements of the invention as described relative to FIG. 4 is that the sensor window (e.g., sensor 401) can be mounted flush within a probe housing or device structure, not shown. As a result, only a flat surface need be placed within the fluid to be tested, thereby discouraging the accumulation or formation of unwanted substances along corners, edges and crevices of the sensing element. This configuration also simplifies cleaning of the sensing surface.

Although the embodiment shown in FIG. 4 utilizes a single sensing surface 407, it should be appreciated that the invention is not limited to single sensing surface configurations. For example, a second preferred embodiment of the invention shown in FIG. 5 utilizes a probe 501 with dual sensing surfaces 503 and 505. During use, probe 501 is inserted into the medium, e.g., seawater, to be investigated. In this configuration a single probe surface 507 provides both the entrance and exit surfaces for the probe. In order to provide the desired level of probe mobility, preferably the probe is coupled to light source 413 and the spectrograph detector 421 via a pair of optical fibers 509 and 511, respectively. Preferably optical fibers 509 and 511 are single mode optical fibers. To provide the desired level of beam collimation, preferably lenses (not shown) are interposed between probe 501 and one or both fibers 509/511.

Figure 5:
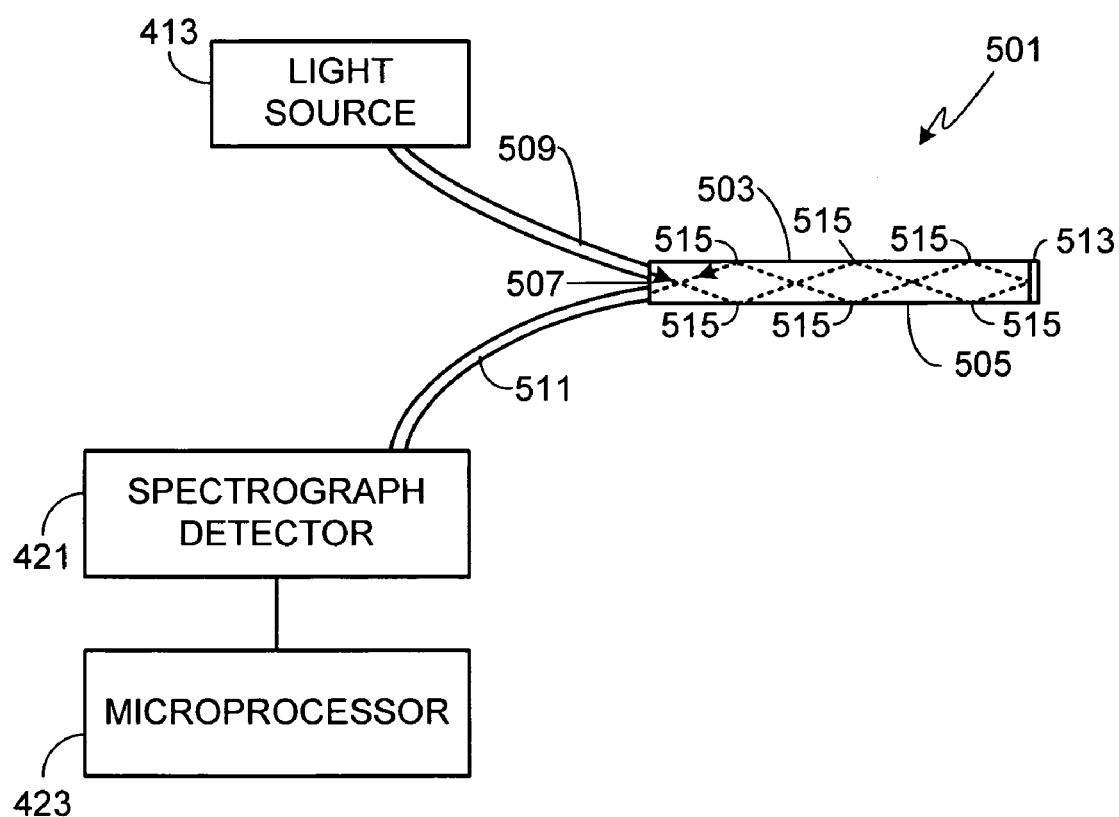
FIG. 5 illustrates an alternate embodiment of a refractometer designed in accordance with the invention, this embodiment providing dual sensing surfaces.

In the embodiment illustrated in FIG. 5, the input light beam is reflected once by sensing surface 503 and twice by sensing surface 505 before being totally reflected by probe end mirror 513. On the return path of the light beam, it is reflected twice by sensing surface 503 and once by sensing surface 505 before exiting the probe. Accordingly, the light beam within probe 501 interacts with the external material to be tested six times at sensing locations 515. It will be appreciated that a probe can be designed for use with the invention that has fewer or greater numbers of sensing locations.

In a device configuration such as that shown in FIG. 5, it is critical that the angle at which the light beam enters the sensor remains constant since changes in the angle of incidence will affect the angle of incidence at the sensing locations and thus the accuracy of the device. Accordingly, in a preferred embodiment the materials comprising optical fiber 509, probe 501 and any optical elements (e.g., collimating lenses) interposed between fiber 509 and prove 501 are all selected to insure that their thermal expansion coefficients match.

In one configuration of probe 501, the probe has a width of 1 millimeter and a length of 7 millimeters. Preferably surfaces 503 and 505 are parallel to one another to within 10 arc seconds. Suitable materials for probe 501 include fuzed quartz, Crown glass and Flint glass, depending upon the desired sensitivity and range.

In another preferred embodiment of the invention, a reference beam is used to monitor variations in light source intensity and/or the spectral distribution of the light source. In the exemplary embodiment illustrated in FIG. 6, which is based on the configuration shown in FIG. 4, a reference beam 601 of primary light beam 603 is split off, preferably using a polarizing beam splitter 605. Reference beam 601, after bypassing sensor 401, is directed to spectrograph 421, aligning the reference beam with sensor beam 607. Preferably the alignment of reference beam 601 is accomplished with the combination of a mirror 609 and a second polarizing prism 611.

Figure 6:
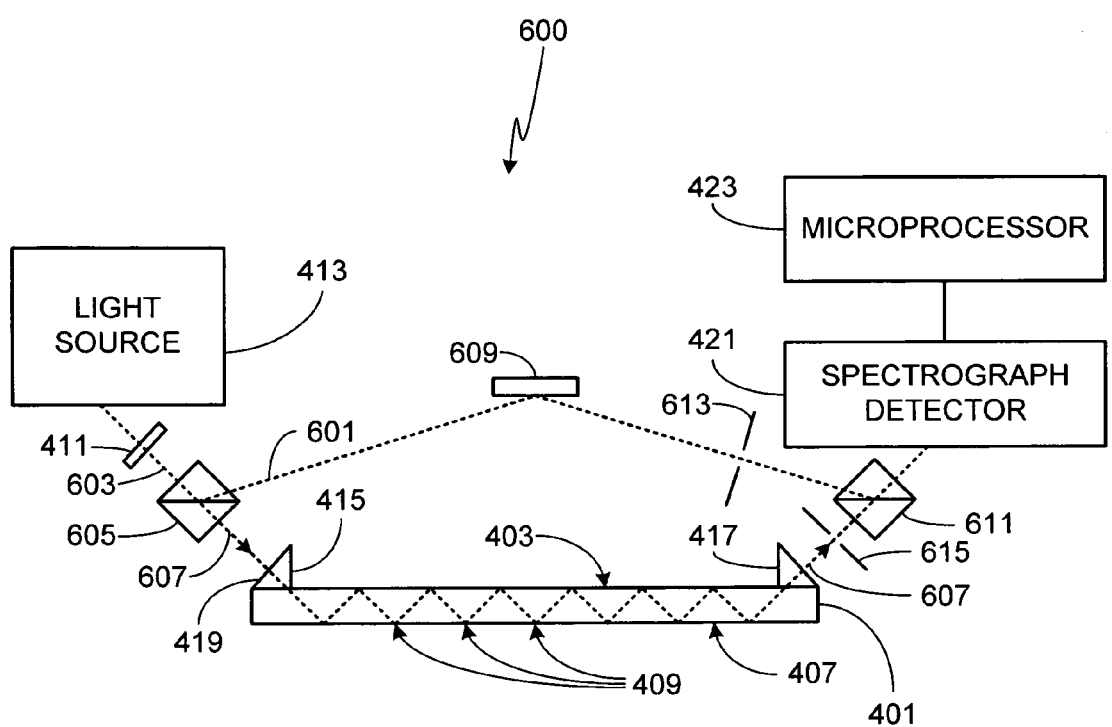
FIG. 6 illustrates a variation of the configuration shown in FIG. 4, this variation providing a reference beam to monitor intensity and spectral variations in the light source.

In order to utilize the reference beam of the embodiment shown in FIG. 6, means such as a shutter are used to control both the reference beam (e.g., shutter 613) and the sensing beam (e.g., shutter 615). Under normal conditions when the system is being used to measure the index of refraction of seawater or some other substance, reference beam 601 is prevented from entered spectrograph 421, for example by closing shutter 613, while sensing beam 607 passes unimpeded to spectrograph 421, for example by opening shutter 615. Conversely, when a normalizing spectrum is desired, the sensing beam shutter is closed and the reference beam shutter is opened.

As previously noted, preferably if the system of the invention uses a reference beam in order to compensate for light source drift as described relative to system 600, the reference beam is generated using a polarizing beam splitter (e.g., polarizing beam splitter prism 605). By using polarizing beam splitters, the p-polarization (i.e., the polarization parallel to the plane of incidence) passes through polarizing prism 605 and is transmitted to sensor 401 and thus sensing surface 407 while the s-polarization (i.e., the polarization perpendicular to the plane of incidence) becomes the reference beam 601. Since the slope and the rate of beam intensity change near the critical reflection wavelength of a p-polarized beam is twice that of an s-polarized beam, an additional benefit of system 600 using polarizing beam splitters is that the sensitivity of the index of refraction measurement is increased by a factor of two over the non-polarized approach. It will be appreciated that the use of a p-polarized beam can also be used to increase the sensitivity of a conventional, i.e., single reflection, critical wavelength refractometer.

Figure 7:
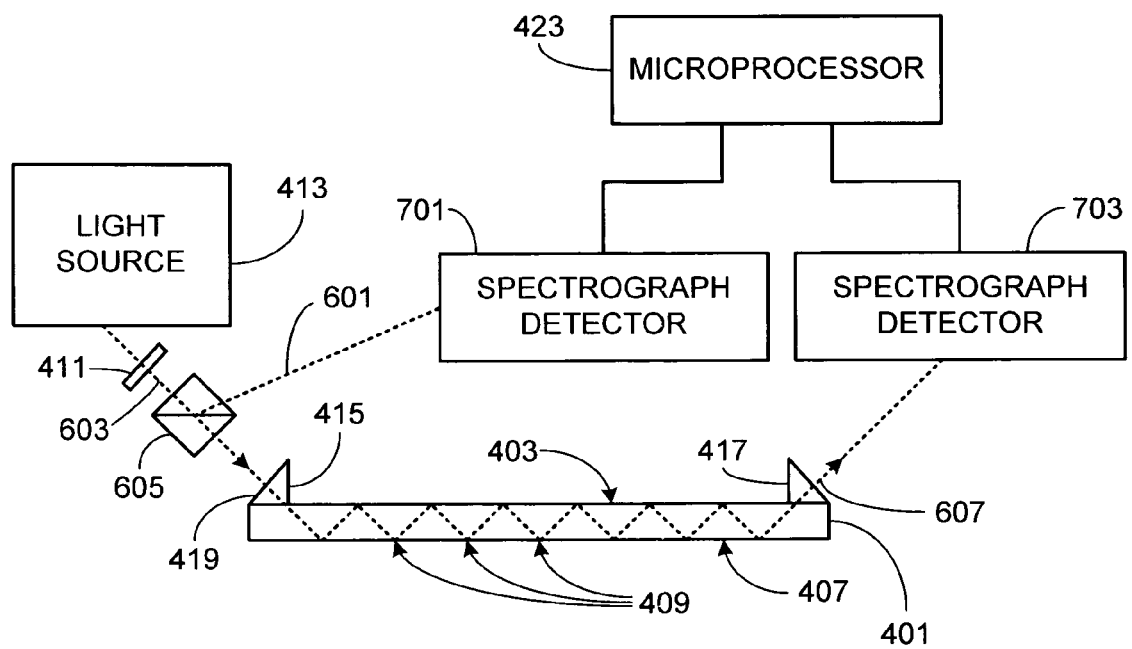
FIG. 7 illustrates a variation of the configuration shown in FIG. 6, this variation utilizing two spectrographs.

In system 600, shutters 613 and 615 allow multiplexing of the reference beam and the sensing beam with single spectrometer 421. If desired and as illustrated in FIG. 7, a pair of spectrometers 701 and 703 can be used with the reference and sensing beams, respectively. Accordingly, the use of dual spectrometers allows light source intensity and wavelength variations to be continuously monitored, thereby providing means for continuously compensating for the effects of such variations on the measured data.

Figure 8:
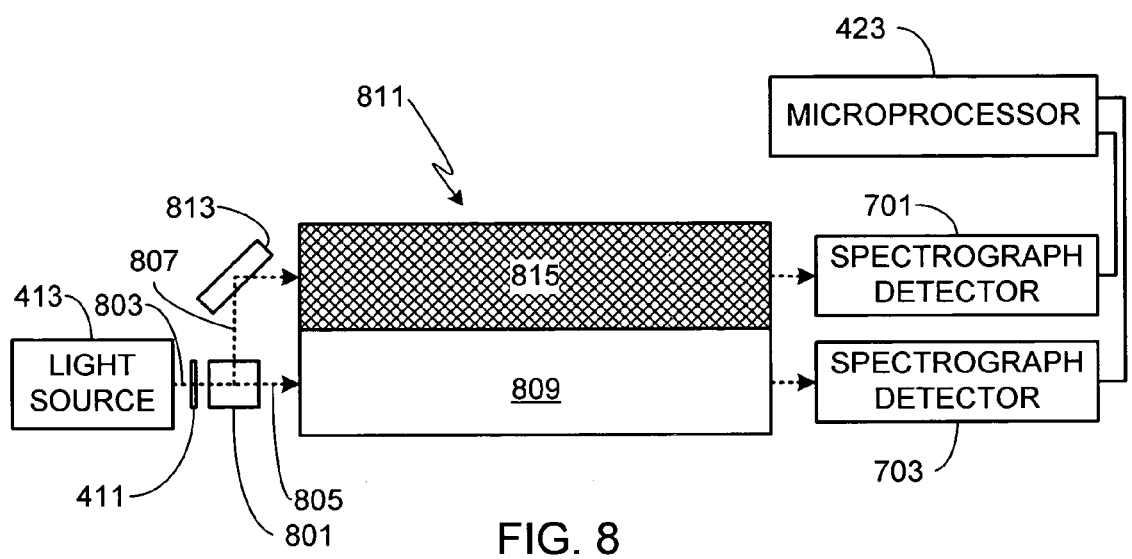
FIG. 8 illustrates a variation of the configuration shown in FIG. 4, this variation dividing the sensor into a sensing portion and a reference portion.

It is understood that there are numerous optical techniques that can be used to direct the light beams; both the sensing light beam before and after it passes through the sensor and the reference light beam, assuming the configuration in question employs a reference light beam. For example, if the desired device configuration utilizes a reference beam to compensate for light source variations as described relative to FIGS. 6 and 7 and to compensate for some environmental variations such as temperature, the reference beam optical path can be directed through a non-sensing portion of the sensor. FIG. 8 shows a top view of the primary elements of such a configuration.

As shown in FIG. 8, the broadband light from source 413 passes through a beam splitting element 801, thereby dividing incident beam 803 into sensing beam 805 and reference beam 807. Sensing beam 805 passes through portion 809 of sensor 811, undergoing multiple reflections (not shown) against the sensing surface(s) of sensor 811, for example as shown relative to the multi-reflection paths shown in FIGS. 6 and 7. Reference beam 807 is directed, for example by a mirror 813, into a second portion 815 of sensor 811. Instead of having a sensing surface, portion 815 is mirrored so that reference beam 807 passes through sensor 811 unaffected by the seawater or other material in contact with the sensor. After passing through sensor 811, reference beam 807 and sensing beam 805 are directed into a pair of spectrographs 701 and 703, respectively. Alternately, both the reference beam and the sensing beam can use a single spectrograph (not shown), for example by using shutters as described relative to FIG. 6.

Preferably in the embodiment illustrated in FIG. 8 beam splitting element 801 is a polarizing splitter. In such a configuration, and as described above, preferably after passing through element 801, sensing beam 805 is p-polarized while reference beam 807 is s-polarized.

It will be appreciated that a refractometer designed and fabricated in accordance with the invention can be used alone, or in combination with other test instruments to provide further information about the material (e.g., seawater) under test. For example, a refractometer in accordance with the invention can be combined with a conductivity cell to provide information regarding water contamination, etc.

As used herein, the terms light and light beam refer to electromagnetic radiation comprised of ultraviolet and/or visible and/or infrared radiation.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A critical wavelength refractometer comprising:
    a broadband light source;
    a sensor, wherein an entrance face of said sensor is optically coupled to said broadband light source, said sensor comprised of at least one sensing surface, wherein light emitted by said broadband light source and optically coupled to said sensor undergoes a plurality of internal reflections within said sensor, wherein a portion of said plurality of internal reflections are against said at least one sensing surface, wherein said portion is comprised of multiple reflections, and wherein for each of said multiple reflections a first fraction of said light is reflected from said sensing surface and a second fraction of said light passes through said sensing surface, wherein said first and second fractions of said light are a function of an index of refraction of a material in contact with said at least one sensing surface;
    a detector optically coupled to an exit face of said sensor, said detector measuring spectral intensity for said first fraction of said light passing through said sensor and exiting through said exit face of said sensor; and
    a microprocessor coupled to said detector, said microprocessor determining a critical wavelength for said material and said index of refraction for said material from said spectral intensity.

2. The critical wavelength refractometer of claim 1, said sensor further comprising a sensor window, wherein said at least one sensing surface comprises a lower surface of said sensor window, and wherein an upper surface of said sensor window and said lower surface are parallel to within 10 arc seconds.

3. The critical wavelength refractometer of claim 1, said sensor further comprising a sensor window, a first prism and a second prism, wherein said broadband light source is optically coupled to said entrance face of said sensor via said first prism, and wherein said detector is optically coupled to said exit face of said sensor via said second prism.

4. The critical wavelength refractometer of claim 1, said sensor further comprising a sensor probe, wherein said at least one sensing surface comprises a lower surface and an upper surface of said sensor probe, wherein an end surface of said sensor probe is mirrored, wherein said entrance face of said sensor is comprised of a first portion of a front surface of said sensor probe, and wherein said exit face of said sensor is comprised of a second portion of said front surface of said sensor probe.

5. The critical wavelength refractometer of claim 1, wherein said detector is a spectrograph.

6. The critical wavelength refractometer of claim 1, further comprising an optical collimator interposed between said broadband light source and said sensor.

7. The critical wavelength refractometer of claim 1, further comprising a first optical fiber interposed between said broadband light source and said sensor and a second optical fiber interposed between said sensor and said detector.

8. The critical wavelength refractometer of claim 1, wherein said sensor is fabricated from a material selected from the group consisting of silica, crown glass, flint glass and germanium doped silica.

9. The critical wavelength refractometer of claim 1, further comprising:
    a beam splitter interposed between said broadband light source and said sensor, wherein said beam splitter divides said light from said broadband light source into a reference beam and a sensing beam, wherein said sensing beam is optically coupled to said sensor; and
    a second detector, wherein said reference beam is optically coupled to said second detector, said second detector measuring spectral intensity for said reference beam, and wherein said microprocessor is coupled to said second detector.

10. The critical wavelength refractometer of claim 9, wherein said beam splitter is a polarizing beam splitter.

11. The critical wavelength refractometer of claim 1, further comprising:
    a beam splitter interposed between said broadband light source and said sensor, wherein said beam splitter divides said light from said broadband light source into a reference beam and a sensing beam, wherein said sensing beam is optically coupled to said sensor, and wherein said reference beam is optically coupled to said detector;
    a first shutter interposed between said beam splitter and said detector, wherein said first shutter controls entry of said sensing beam to said detector; and
    a second shutter interposed between said beam splitter and said detector, wherein said second shutter controls entry of said reference beam to said detector.

12. The critical wavelength refractometer of claim 11, wherein said beam splitter is a polarizing beam splitter.

13. The critical wavelength refractometer of claim 11, wherein said first shutter is interposed between said sensor and said detector.

14. The critical wavelength refractometer of claim 11, further comprising optical means for coupling said reference beam to said detector, said optical means comprising at least one mirror and at least one beam combiner.

15. The critical wavelength refractometer of claim 1, said sensor further comprising a sensor window, wherein said at least one sensing surface comprises a first portion of a lower surface of said sensor window, and wherein a second portion of said lower surface of said sensor window is mirrored, wherein said critical wavelength refractometer further comprises:
- a beam splitter interposed between said broadband light source and said sensor, wherein said beam splitter divides said light from said broadband light source into a reference beam and a sensing beam, wherein said sensing beam is optically coupled to said first portion of said lower surface of said sensor window, and wherein said reference beam is optically coupled to said second portion of said lower surface of said sensor window; and
- a second detector, wherein said reference beam is optically coupled to said second detector, said second detector measuring spectral intensity for said reference beam, and wherein said microprocessor is coupled to said second detector.

16. The critical wavelength refractometer of claim 15, wherein said beam splitter is a polarizing beam splitter.

17. The critical wavelength refractometer of claim 1, said sensor further comprising a sensor window, wherein said at least one sensing surface comprises a first portion of a lower surface of said sensor window, and wherein a second portion of said lower surface of said sensor window is mirrored, wherein said critical wavelength refractometer further comprises:
- a beam splitter interposed between said broadband light source and said sensor, wherein said beam splitter divides said light from said broadband light source into a reference beam and a sensing beam, wherein said sensing beam is optically coupled to said first portion of said lower surface of said sensor window, and wherein said reference beam is optically coupled to said second portion of said lower surface of said sensor window, and wherein said reference beam is optically coupled to said detector;
- a first shutter interposed between said first portion of said lower surface of said sensor window and said detector, wherein said first shutter controls entry of said sensing beam to said detector; and
- a second shutter interposed between said second portion of said lower surface of said sensor window and said detector, wherein said second shutter controls entry of said reference beam to said detector.

18. The critical wavelength refractometer of claim 17, wherein said beam splitter is a polarizing beam splitter.

19. A method of determining an index of refraction of a material in contact with a sensing surface of a sensor, the method comprising the steps of:
- transmitting a light beam from a broadband light source into said sensor, said sensor having a second index of refraction;
- fixing an angle of incidence of said light beam relative to said sensor, wherein said light beam undergoes multiple internal reflections against said sensing surface of said sensor, wherein each of said multiple internal reflections against said sensing surface provides a separate sensing location, wherein said material is in contact with said sensing surface of said sensor;
- transmitting said light beam exiting from said sensor to a spectrographic detector, said spectrographic detector measuring light intensity as a function of wavelength for said light beam exiting said sensor;
- monitoring the light intensity as a function of wavelength for said light beam exiting from said sensor with said spectrographic detector;
- determining a critical wavelength corresponding to said light beam exiting from said sensor; and
- determining the index of refraction of said material from said critical wavelength, said angle of incidence, and said second index of refraction corresponding to said sensor.

* * * * *